United States Patent [19]

MacCoss et al.

[11] Patent Number: 4,980,350
[45] Date of Patent: Dec. 25, 1990

[54] PIPERAZINYLALKYLPYRIMIDINES AS HYPOGLYCEMIC AGENTS

[75] Inventors: Malcolm MacCoss, Freehold; Richard L. Tolman, Warren; Arthur F. Wagner, Princeton, all of N.J.

[73] Assignee: Merck & Co., Inc., Rahway, N.J.

[21] Appl. No.: 387,198

[22] Filed: Jul. 31, 1989

Related U.S. Application Data

[63] Continuation of Ser. No. 160,454, Feb. 25, 1988, abandoned.

[51] Int. Cl.$^5$ ............... A61K 31/495; A61K 31/505; A61K 31/53; C07D 403/04
[52] U.S. Cl. .................................. 514/245; 514/252; 544/295; 544/198; 544/207; 544/209; 544/212
[58] Field of Search .................. 544/7, 8, 55, 58.6, 544/60, 96, 113, 114, 121, 198, 209, 212, 295, 207; 514/222.2, 222.5, 223.8, 226.2, 235.8, 245, 252

[56] References Cited

U.S. PATENT DOCUMENTS 3,95,384  8/1976  Narr et al. .................. 260/243 R
3,299,067 1/1967 Regnier et al. .................. 514/929

FOREIGN PATENT DOCUMENTS 1297610  6/1969  Fed. Rep. of Germany .
1191465  5/1970  United Kingdom .

OTHER PUBLICATIONS

Sekiya et al *Chem and Pharm Bull* 31 pp. 2254-2261 (1983).
Ohno et al *Chem and Pharm Bull* 34 pp. 4150-4165 (1986).
Nakanishi et al *Chemical Abstracts* 24 141881C (1971).
Benge et al. Journal of Pharmaceutical Sciences vol. 66, No. 1 (1977) pp. 1-19.

*Primary Examiner*—John M. Ford
*Attorney, Agent, or Firm*—Hesna J. Pfeiffer; David L. Rose

[57] ABSTRACT

Novel hypoglycemic agents having the formula (I) are disclosed.

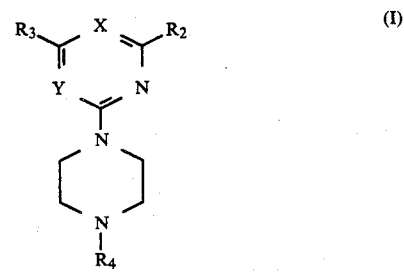

23 Claims, No Drawings

PIPERAZINYLALKYLPYRIMIDINES AS HYPOGLYCEMIC AGENTS

This is a continuation of application Ser. No. 160,454, filed Feb. 25, 1988, now abandoned.

BACKGROUND OF THE INVENTION

Diabetes is a condition characterized by abnormal insulin secretion and a variety of metabolic and vascular manifestations reflected in a tendency toward inappropriately elevated blood glucose levels and which if left poorly treated or untreated can result in accelerated, nonspecific atherosclerosis, neuropathy and thickened capillary lamina causing renal and retinal impairment. Diabetes is characterized as being insulin dependent (Type I) and non-insulin dependent (Type II). Type I diabetes is due to damage and eventual loss of the β-cells of the pancreatic islets of Langerhans with a resulting loss of insulin production. Type II diabetics secrete insulin, however, the insulin is somehow not properly or effectively utilized in the metabolism of blood sugars and glucose accumulates in the blood to above normal levels. This condition is termed insulin resistance.

With the certainty of serious complications resulting from high glucose levels in poorly controlled or uncontrolled diabetics, means to lower blood glucose have been research goals for a considerable period of time. With Type I diabetes glucose control can, at present, only be achieved with daily insulin injections. With Type II diabetes glucose control can be effected from a combination of diet and drugs which lower glucose levels. The currently available oral hypoglycemic agents are not completely satisfactory since they may not offer complete blood glucose control or may provide a variety of undesirable side effects or they may elevate insulin concentrations to undesirable and dangerous levels. Thus, the search for improved oral hypoglycemic agents is a continuing one.

The compounds of the present invention are piperazinylalkylpyrimidines. The literature discloses a number of piperazinylpyrimidines which are structurally distinct from the present compounds and generally have no disclosed hypoglycemic activity.

EP No. 115,714-A discloses 2-piperazinylpyrimidines of structural formula:

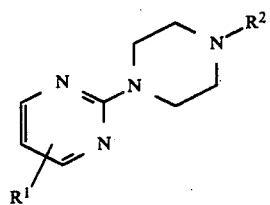

where $R^1$=H or hydroxy; and $R^2$=H or $C_{1-6}$ alkyl. These derivatives do not bear alkyl substituents on the pyrimidine ring and are structurally distinct from the instant compounds and have no disclosed hypoglycemic activity.

Japanese publication No. J5,0058 082 discloses piperazinylpyrimidines of structural formula:

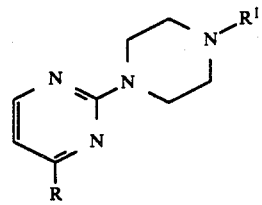

wherein $R^1$=H, alkyl, alkanoyl or PhCH$_2$; and R is halo or $R^2$NH; $R^2$ is H or alkyl. These substituted pyrimidines do not contain alkyl substituents directly bonded to the pyrimidine ring and are structurally distinct from the instant compounds.

U.S. Pat. No. 4,409,223 discloses 2-piperazinylpyrimidines of structural formula:

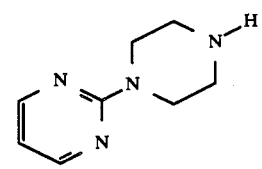

These unalkylated pyrimidines, are structurally distinct from the instant compounds and have no disclosed hypoglycemic activity.

DE No. 3321969 discloses 2-piperazinylpyrimidines of structural formula

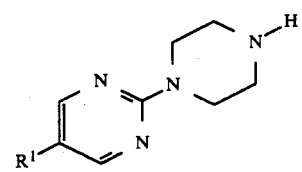

wherein among other groups $R^1$ =H or optionally substituted alkyl. These compounds were disclosed as intermediates in the further preparation of compounds substituted on the piperazine ring which have CNS activity.

U.S. Pat. No. 3,299,067 discloses 2-piperazinylpyrimidines of structural formula:

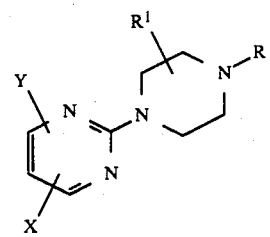

wherein R is a benzyl or phenyl moiety, $R^1$ is H or CH$_3$, and X and Y among other groups are H or lower alkyl. These aryl substituted piperazinylpyrimidines are structurally distinct from the instant compounds.

DESCRIPTION OF THE INVENTION

This invention relates to new hypoglycemic compounds having the structural formula (I):

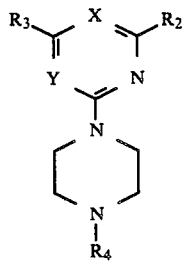

wherein
X and Y are independently —N= and —(C—$R_1$)=; provided that at least one of X or Y is —N=;
$R_1$ is H, $C_{1-6}$alkyl, halo$C_{1-6}$alkyl, dihalo$C_{1-6}$alkyl or $C_{1-6}$alkoxy;
$R_2$ and $R_3$ are independently H, $C_{1-6}$alkyl, halo$C_{1-6}$alkyl, dihalo$C_{1-6}$alkyl, $NH_2$, $NR_5R_6$, $C_{1-6}$alkoxy, provided that only one of $R_2$ and $R_3$ may be H and when $R_2$ or $R_3$ is $NH_2$ or $NR_5R_6$ X is —N=;
$R_4$ is H, $C_{1-6}$alkyl, $C_{6-10}$aryl$C_{1-6}$alkyl, $C_{2-6}$alkenyl, $C_{2-6}$alkynyl;
$R_5$ and $R_6$ are independently H, $C_{1-6}$alkyl or $R_5$ and $R_6$ together with the nitrogen atom to which they are attached form a heterocyclic ring of 5 to 6 atoms;
halo is Br, Cl or F.

It should be understood that the alkyl, haloalkyl alkoxy, alkenyl and alkynyl groups of this invention may either be in a straight chain or branched configuration.

The amino and substituted amino groups are exemplified by amino, methylamino, dimethylamino, ethylamino, diethylamino, pyrrolidino, morpholino, propylamino, and the like.

One embodiment of the present invention relates to those compounds of formula (I) wherein
X is —(C—$R_1$)=;
Y is —N=;
$R_1$ is H, $C_{1-6}$alkyl, halo$C_{1-6}$alkyl, dihaloalkyl, or $C_{1-6}$alkoxy;
$R_2$ is H, or $C_{1-6}$alkyl, haloalkyl or dihaloalkyl;
$R_3$ is H, or $C_{1-6}$alkyl, haloalkyl or dihaloalkyl; provided that only one of $R_2$ and $R_3$ may be H;
$R_4$ is H, or $C_{1-6}$alkyl.

In one class of this embodiment are those compounds wherein:
$R_1$ is H, $C_{1-6}$alkyl, or $F_2C_{1-6}$alkyl;
$R_2$ is H, $C_{1-6}$alkyl, $FC_{1-6}$alkyl or $F_2C_{1-6}$alkyl;
$R_3$ is H, $C_{1-6}$alkyl, $FC_{1-6}$alkyl or $F_2C_{1-6}$alkyl; provided that only one of $R_2$ and $R_3$ may be H.

The fluoroalkyl derivatives of this class are preferably $FCH_2CH_2$— and $F_2CHCH_2$—, most preferably $FCH_2CH_2$—.

In a subclass:
$R_1$ is H or $CH_3$;
$R_2$ is $C_{1-6}$alkyl; and
$R_3$ is H or $C_{1-6}$alkyl.

Exemplifying this subclass are those compounds wherein:
a. $R_1$=H, $R_2$=n butyl, $R_3$=methyl and $R_4$=H.
b. $R_1$=H, $R_2$=sec butyl, $R_3$=H, and $R_4$=H.
c. $R_1$=methyl, $R_2$=methyl, $R_3$=H, and $R_4$=H.
d. $R_1$=H, $R_2$=methyl, $R_3$=H, and $R_4$=H.
e. $R_1$=H, $R_2$=methyl, $R_3$=methyl and $R_4$=H.
f. $R_1$=H, $R_2$=methyl, $R_3$=H, and $R_4$=methyl.
g. $R_1$=methyl, $R_2$=methyl, $R_3$=methyl, $R_4$=H.

A second embodiment of the present invention relates to those compounds of formula (I) wherein:
X is —N=;
Y is —(C $R_1$)=;
$R_1$ is H, $C_{1-6}$alkyl, halo$C_{1-6}$alkyl, dihalo$C_{1-6}$alkyl or $C_{1-6}$alkoxy;
$R_2$ is H, or $C_{1-6}$alkyl, halo$C_{1-6}$alkyl, dihalo$C_{1-6}$alkyl, $NH_2$ or $NR_5R_6$;
$R_3$ is H, or $C_{1-6}$alkyl, halo$C_{1-6}$alkyl, dihalo$C_{1-6}$alkyl; provided that only one of $R_2$ and $R_3$ may be H;
$R_4$ is H, or $C_{1-6}$alkyl.

In a class of this embodiment are those compounds wherein:
$R_1$ is H or $C_{1-6}$alkyl, $FC_{1-6}$alkyl, $F_2C_{1-6}$alkyl or $C_{1-6}$alkoxy;
$R_2$ is H or $C_{1-6}$alkyl, $FC_{1-6}$alkyl, $F_2C_{1-6}$alkyl; $NH_2$ or $NR_5R_6$;
$R_3$ is H or $C_{1-6}$alkyl, $FC_{1-6}$alkyl, $F_2C_{1-6}$alkyl; provided that only one of $R_2$ and $R_3$ may be H.

The fluoroalkyl derivatives of this class are preferably $FCH_2CH_2$— and $F_2CH_2CH_2$—, most preferably $FCH_2CH_2$—.

In a subclass
$R_1$ is H or $C_{1-6}$alkyl or $C_{1-6}$alkoxy;
$R_2$ is H or $C_{1-6}$alkyl, $NH_2$ or $NR_5R_6$;
$R_3$ is H or $C_{1-6}$alkyl.

Further illustrating this subclass are the compounds wherein
$R_1$ is H or $C_{1-6}$alkoxy,
$R_2$ is $C_{1-6}$alkyl or $NH_2$; and
$R_4$ is H.

The subclass is exemplified by the compounds wherein
a. $R_1$ is methoxy, $R_2$ is methyl, $R_3$ is H;
b. $R_1$ is H, $R_2$ is $NH_2$, $R_3$ is methyl.

A third embodiment of the present invention relates to those compounds of formula (I) wherein:
X is —N=;
Y is —N=;
$R_2$ is H or $C_{1-6}$alkyl or $FC_{1-6}$alkyl or $F_2C_{1-6}$alkyl;
$R_3$ is H or $C_{1-6}$alkyl or $F_2C_{1-6}$alkyl;
$R_4$ is H or $C_{1-6}$alkyl.

In a class of this embodiment
$R_2$ is H or $C_{1-6}$alkyl; and
$R_3$ is H or $C_{1-6}$alkyl.

Exemplifying this class is the compound wherein:
$R_2$ is methyl, $R_3$ is hydrogen, and $R_4$ is hydrogen.

Piperazinyl or substituted piperazinyl pyrimidines or triazines are formed from the appropriately substituted alkylhalopyrimidine or alkylhalotriazine in a nucleophilic displacement of the halo group by a N-substituted or N-protected piperazine. The starting alkylhalopyrimidine is either commercially available or can be directly prepared from the analogous alkylhydroxypyrimidine by standard reactions using reagents such as phosphorus oxychloride. The alkylhydroxypyrimidines can be prepared by the "Principal Synthesis", a very general route linking a C—C—C fragment with an N—C—N fragment. The "Principal Synthesis" has been described in detail in *The Pyrimidines*, D. J.

Brown, John Wiley and Sons, (1962) and updated in Supplements I (1970) and II (1985). In some examples better yields in the nucleophilic displacement were obtained by using a dihalo substituted pyrimidine starting material and in those cases the unreacted halogen is eventually removed by hydrogenation. The appropriately substituted S-triazines are prepared by standard chemical transformations such as those described in *S triazines*, E. M. Smolin et al. Interscience 1959 and *Structure and Reactions of Heterocyclic Compounds*, M. H. Palmer, St. Martins Press (1967).

Piperazinyl protecting groups such as tert butoxycarbonyl or triphenylmethyl are removed by standard procedures for example trifluoroacetic acid or ethanol HCl for tert butoxycarbonyl and acetone-HCl for triphenylmethyl.

Alkyl groups can be substituted at the 4 or 6- position of a pyrimidine ring using an alkyllithium and a tertiary diamine, such as N,N,N',N'-tetra-methylethylenediamine.

Substituent groups such as alkoxy or amino are readily incorporated onto a pyrimidine ring using the "Principal Synthesis".

Halogenated alkyl groups can be incorporated into the pyrimidine ring using a protected hydroxyalkyl substituent on the amidine moiety or the C—C—C fragment in the "Principal Synthesis". The protecting group is then removed and the hydroxyl group is replaced by reaction with a halogenating agent such as diethylaminosulfur trifluoride (DAST) to yield the haloalkyl derivative which, with DAST, is the fluoroalkyl derivative. Standard halogenation procedures can be used for other halogens.

The compounds of this invention are all readily adapted to therapeutic use as oral hypoglycemic agents. These compounds lower the blood sugar levels of diabetic subjects to a statistically significant degree. For instance, (4-methyl 2 piperazinyl-pyrimidine) a typical and preferred agent of the present invention has been found to consistently lower blood sugar levels and improve glucose tolerance in either fasted or fed diabetic (i.e., hyperglycemic) mice to a statistically significant degree when given by the oral route of administration at dose levels ranging from 1 mg/kg to 100 mg/kg, respectively, without showing any toxic side effects. The other compounds of this invention also produce similar results. In general, these compounds are ordinarily administered at dosage levels ranging from about 1 mg to about 100 mg per kg of body weight per day, although variations will necessarily occur depending upon the condition and individual response of the subject being treated and the particular type of oral pharmaceutical formulation chosen.

Administration over time to obese, insulin resistant mice, resulted in a significant reduction of glucose in a glucose tolerance test.

In connection with the use of the compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tableting purposes. Solid compositions of a similar type may also be employed as fillers in soft and hard filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted or fed hyperglycemic mouse when tested therein for such purposes according to the procedures described by Saperstein et al. as submitted to the journal *Diabetes* and summarized as follows: Genetically obese mice (ob/ob) were fasted overnight;. the compounds were administered orally via a stomach tube and each mouse serially bled from the orbital sinus at various times and the blood samples analyzed for blood glucose. When the effects of the compounds on blood glucose levels were to be determined, glucose was administered orally at a rate of 2 g per kg. 30 minutes after administration of the test compound. Glucose in the blood was determined by the potassium ferricyanide potassium ferrocyanide oxidation reaction auto analyzer.

The latter method measures directly the amount of glucose in the blood at any given time and from this, the maximum percent decrease in blood sugar can be readily calculated and reported as hypoglycemic activity per se. In this way, the present compounds are shown to markedly improve glucose tolerance of non anesthetized hyperglycemic mice when administered to them at dose levels as low as 10 mg/kg orally and lower fasting blood glucose levels when administered at dose levels as low as 30 mg/kg orally.

The instant invention is further described by the following examples which are intended to be merely descriptive and should not be construed as limitative of the invention.

EXAMPLE 1

Preparation of 4-methyl-2-(1-piperazinyl)pyrimidine dihydrochloride (a) 2-[1-(4-tert-butoxycarbonylpiperazinyl)]-4-chloro-6-methylpyrimidine 2,4-Dichloro-6-methylpyrimidine (2.0 q, 12.3 mmol) and 1 tert-butoxycarbonylpiperazine (1-BOC piperazine) (4.8 g, 25.8 mmol) were dissolved in $CHCl_3$ (50 ml) and the mixture was heated under reflux for 45 minutes and then allowed to cool to room temperature. After standing for 3 hours, $H_2O$ was added and the precipitated material (2.9 g) was filtered off. The filtrate was extracted with 10% aqueous $Na_2CO_3$, dried ($MgSO_4$), filtered and then evaporated to dryness. TLC (silica, $CH_2Cl_2$-MeOH, 97:3) showed the title compound (higher Rf) and its regioisomer 4-[1-(4-BOC) piperazinyl)]-2-chloro-6-methylpyrimidine (lower Rf) as the main products. These were separated on a silica gel 60 column (5×13 cm) developed with $CH_2Cl_2$ and then $CH_2Cl_2$-MeOH(99:1) to give the title compound. Confirmation of regioisomerism was obtained from CMR and PMR.

Calculated for: $C_{14}H_{21}N_4O_2Cl$: C, 53.76; H, 6.77; N, 17.91. Found C, 53.97; H, 6.69; N, 17.82.

(b) 2-[1-(4-BOC)piperazinyl]-4-methylpyrimidine

The material prepared in part (a) (500 mg, 1.6 mmol) was dissolved in EtOH (25 ml) and hydrogenated at 2.5 psi over 5% Pd/C (100 mg) and MgO (150 mg) overnight. The mixture was filtered through Celite and the filtrate was evaporated to an off white foam (462 mg). This was further purified on a column of silica gel 60 (2×10 cm), developed with $CH_2Cl_2$-MeOH(9:1).

Fractions containing the required product were pooled and evaporated to an oil which crystallized slowly on standing.

(c) 4-Methyl-2-(1-piperazinyl)pyrimidine dihydrochloride

The material prepared in part (b) (167 mg, 0.60 mmol) was dissolved in $CF_3COOH$ (10 ml) and after 1.5 hour the mixture was concentrated to dryness under a stream of $N_2$. The gum was dissolved in MeOH and evaporated to dryness (evaporation was repeated several times from MeOH and $H_2O$ to ensure removal of $CF_3COOH$). This residue was dissolved in a little $H_2O$ and passed onto a column of Dowex 1X2 ($OH^-$) (2.5×22 cm) developed with $H_2O$. Fractions containing the required product were pooled and evaporated to dryness to give 97 mg of a colorless solid. This was dissolved in EtOH (3 ml) and an excess of methanolic HCl was added. The solution was concentrated under a stream of $N_2$ and the residue was redissolved in EtOH (2 ml). Crystals of the title compound formed on standing and these were collected by centrifugation, washed with EtOH (3×0.5 ml), and dried in vacuo.

Calculated for $C_9H_{14}N_4.2HCl$: C, 43.04; H, 6.42; N, 22.31. Found: C, 43.09; H, 6.40; N, 22.14.

EXAMPLE 2

Preparation of 4,5-Dimethyl-2-(1-piperazinyl)-pyrimidine-hydrochloride (a) 2-[1-(4-BOC)piperazinyl]-6-chloro-4,5-dimethylpyrimidine To a stirred solution of 2,4-dichloro-5,6-dimethylpyrimidine (1.00 g, 5 65 mmol) in $CHCl_3$ (25 ml) at 0°, under $N_2$, was added a solution of 1-BOCpiperazine (4.22 g, 22.69 mmol) in $CHCl_3$ (10 ml). This solution was stirred successively at 0° for 1 hour, then room temperature for 1 hour, and then at 50°-60° for 7 hours. The mixture was then cooled to room temperature and extracted with 10% aqueous $Na_2CO_3$ (3×50 ml). The organic phase was dried ($MgSO_4$), filtered and evaporated to dryness to give a mixture of the title compound (higher Rf in (EtOAc-hexanes 1:5) and 6-[1-(4-BOC)-piperazinyl)]-2-chloro-4,5-dimethylpyrimidine which were separated by chromatography on silica gel 60 (5×10.5 cm), developing with a step gradient of $CH_2Cl_2$ to $CH_2Cl_2$-MeOH (9:1). The title compound was obtained chromatographically pure as a white residue and the regioisomerism was confirmed by CMR and PMR.

(b) 2-[1-(4-BOC)piperazinyl]-4,5-dimethylpyrimidine

The material prepared in part (a) (467 mg, 1.43 mmol) was dissolved in EtOH (25 ml) and hydrogenated at 2.5 psi over 5%. Pd/C (90 mg) and MgO (130 mg) overnight. The mixture was filtered through Celtite and the filtrate was evaporated to dryness. This residue was purified on a silica gel 60 column (13×30 cm) developed with $CH_2Cl_2$, $CH_2Cl_2$-MeOH (99:1), and then $CH_2Cl_2$-MeOH (98:2). Fractions containing the title compound were pooled and evaporated to dryness to give the product as a chromatographically pure white residue.

(c) 4,5-Dimethyl-2-(1-piperazinyl)pyrimidine hydrochloride

The material prepared in part (b) (270 mg, 0.92 mmol) was dissolved in $CF_3COOH$ (7 ml) and after 1 hour, the mixture was concentrated under a stream of $N_2$. The residue was evaporated to dryness in vacuo 2× from MeOH and then 2× from $H_2O$ and this material was dissolved in a minimum amount of $H_2O$ and passed down a Dowex 1×2 ($OH^-$) column (2.5×25 cm) developed with $H_2O$. The major peak was collected and evaporated to dryness (170 mg) and this residue was dissolved in MeOH and methanolic HCl was added. After concentrating to 1 ml under a stream of $N_2$, the white solid was removed by centrifugation, washed with cold EtOH (3×2 ml) and dried in vacuo.

Calculated for C$_{10}$H$_{16}$N$_4$·HCl: C, 52.51; H, 7.49; N, 24.50; Cl, 15.50. Found: C, 52.52; H, 7.38; N, 24.44; Cl, 15.41.

EXAMPLE 3

Preparation of 4,6-Dimethyl-2-(1-piperazinyl)-pyrimidine-dihydrochloride (a) 2-[1-(4-BOC)piperazinyl]-4,6-dimethylpyrimidine 2-Chloro-4,6-dimethylpyrimidine (554 mg, 3.89 mmol) and (1-BOC)piperazine were mixed in EtOH (25 ml) and heated under reflux under N$_2$ overnight. Additional (1-BOC)piperazine (230 mg) was added and the reaction continued. Further (1-BOC)piperazine (1.0 g) was added after an additional 3 hours and the reflux was continued for another 24 hours. The mixture was evaporated to dryness in vacuo and the residue was dissolved in CH$_2$Cl$_2$ (50 ml) and extracted with 10% aqueous Na$_2$CO$_3$. The organic phase was dried (MgSO$_4$), filtered and evaporated to dryness. This residue was purified on a silica gel 60 column (3×11 cm) developed with EtOAc hexanes (1:3). Fractions containing the required product were pooled and evaporated to dryness to give the title compound as a white solid. Mass spec. showed M+ at 292 m/e.

(b) 4,6-Dimethyl-2-(1-piperazinyl)pyrimidine dihydrochloride

The material prepared in part (a) (500 mg, 1.78 mmol) was deblocked with CF$_3$COOH, converted to free base using Dowex 1×2 (OH) and then isolated as a dihydrochloride salt using the usual methods described in Examples 1 and 2 part (c). Mass spec. showed M+ (free base) at 192 m/e.

Calculated for C$_{10}$H$_{16}$N$_4$·2HCl·H$_2$O: C, 42.40; H, 7.12; N, 19.78. Found: C, 42.37; H, 6.80; N, 19.64.

EXAMPLE 4

Preparation of 4,5,6-Trimethyl-2-(1-piperazinyl)-pyrimidine dihydrochloride (a) 2 Hydroxy-4,5,6-trimethylpyrimidine To 3.65 g (32 mmol) of 3-methyl-2,4-pentanedione in ethanol (15 ml) was added urea (1.92 g; 32 mmol) followed by 3 drops concentrated HCl. This mixture was refluxed under N$_2$ overnight (12 hours). Upon cooling a solid separated which was filtered off and washed with cold ethanol and ethyl ether. Drying on the pad gave an off-white tlc pure solid. NMR (d$_6$-DMSO, δ from TMS): 1.94(S, 5-CH$_3$), 2.22(S, 4, 6 -CH$_3$S), 5.47 (br S, OH). Mass spectroscopy showed M+ at m/e 138.

(b) 2-Chloro-4,5,6-trimethylpyrimidine 0.8489 g (6.15 mmol) of the compound of part (a) was suspended in POCl$_3$ (5 ml) and heated under reflux under a Drierite guard tube. Complete dissolution did not occur after 1½ hours and so Et$_2$NPh (0.5 ml) was added and the reflux was continued for an additional 1½ hours. Complete solution had occurred to give a wine colored solution. This was concentrated in vacuo to ~2 ml and then added dropwise to ice-H$_2$O (50 ml). The pH of the mixture was adjusted to 3–4 (pH paper) with NH$_4$OH and the solution was extracted with CH$_2$Cl$_2$ (2×50 ml). The pooled organic phases were dried (MgSO$_4$), filtered, and evaporated to an off-white residue. This solid was dissolved in CH$_2$Cl$_2$-MeOH and adsorbed onto a little silica gel by evaporation. The solid was placed atop a dry-packed silica gel 60 column (2.5×33.0 cms) and development was initiated with EtOAc:hexanes 1:3 (500 ml). Then, EtOAc:hexanes 1:1 was utilized; fractions containing the required product, were pooled and evaporated to dryness in vacuo to give the title compound as crystalline plates. NMR (CDCl$_3$, δ from TMS): 2.23 (S, 5-CH$_3$), 2.50 (S, 4.6-CH$_3$'S).

Mass spectroscopy showed the M+ peak at 156.

Anal Calcd for C$_7$H$_9$N$_2$Cl$_1$: C, 53.68; H, 5.79; N, 17.89. Found: C, 53.73; H, 5.75; N, 17.70.

(c) 2-[1-(4-BOC)piperazinyl]-4,5,6-trimethylpyrimidine 400 mgs (2.56 mmol) of the compound from part (b) was dissolved in isoamyl alcohol (10 ml) and 1-BOC-piperazine (1.90 g, 10.2 mmol) was added. This solution was heated under reflux under N$_2$ for 12 hours and then allowed to remain at room temperature for 48 hours. TLC (silica, EtOAc:hexanes 25:75) indicated complete reaction, and the mixture was evaporated to dryness. The residue was dissolved in 10% Na$_2$CO$_3$ (50 ml):CH$_2$Cl$_2$ (50 ml) and the layers were separated. The aqueous phase was further washed with CH$_2$Cl$_2$(2×50 ml) and the pooled organic layers were dried (MgSO$_4$), filtered, and evaporated to dryness. The residue was dissolved in CH$_2$Cl$_2$ and adsorbed onto silica gel 60 and placed atop a dry packed silica gel 60 column (20×26.0 cms). Elution was with EtOAc:hexanes 25:75 and fractions containing pure (tlc) material were pooled and evaporated in vacuo to a pale yellow oil. This crystallized on standing to give crystals after drying in vacuo. Mass spectroscopy showed the M+ peak at 306.

Anal Calc'd for C$_{16}$H$_{26}$N$_4$O$_2$: C, 62.72; H, 8.55; N, 18.29. Found: C, 62.87; H, 8.37; N, 18.09.

(d) 4,5,6-Trimethyl- 2-(1-piperazinyl)pyrimidine dihydrochloride 503.8 mgs of the compound of part (C) was dissolved in CF$_3$COOH. (15 ml) and allowed to remain at room temperature for 45 minutes. The mixture was blown down under N$_2$ and then was evaporated to dryness 2× in vacuo from H$_2$O. The brown residue was dissolved in a little H$_2$O and passed down a Dowex 1×2 (OH$^-$) column (1.5×33.0 cms), developed in H$_2$O. Fractions containing the required product were pooled and evaporated to dryness to give a syrup. This was dissolved in 3 ml EtOH (in a centrifuge tube) and 2 ml of 3.49M HCl in MeOH was added. This solution was allowed to stand at −15° C. overnight. No crystals were formed. The solution was blown down under N$_2$ to ~1 ml, when crystallization occurred ~1 ml EtOH was added and the mixture was chilled to −15° C. before the solid was removed by centrifugation and washed with cold EtOH and Et$_2$O before dying in vacuo to give the title compound as a solid.

Anal. Calc'd for C$_{11}$H$_{18}$N$_4$.2HCl.0.5H$_2$O C, 45.84; H, 7.35, N, 19.44. Found: C, 45.75; H, 7.42; N, 19.31.

EXAMPLE 5

Preparation of
4-Methyl-2-[1-(4-methylpiperazinyl)]-pyrimidine dihydrochloride (a) 2-Chloro-4-methylpyrimidine Method A 2,4-Dichloro-6-methylpyrimidine (20.0 g, 0.12 mol) was suspended in benzene (40 ml) and 5% aqueous $NH_4OH$ saturated with NaCl (100 ml) was added followed by zinc powder (60 g). This mixture was stirred mechanically and heated under reflux for 5 hours and then was allowed to cool to room temperature. Additional benzene was added and the layers were separated; the aqueous layer was further extracted with benzene (80 ml) and the pooled organic layers were dried ($MgSO_4$), filtered and concentrated in vacuo to an oil. This was purified on a silica gel 60 column (630 g) packed in cyclohexane. The column was developed successively with EtOAc:cyclohexane (15:85) and then (30:70) and fractions containing the required product were pooled and evaporated to dryness to give the title compound.

NMR (200 MHz, $CDCl_3$) $\delta$ from TMS: 2.50 (3, s, $CH_3$), 7.10 (1, d, $H_5$ or $H_6$), 8.40 (1, d, $H_6$ or $H_5$).

Calculated for $C_5H_5N_2Cl_1$: C, 46.71; H, 3.92, N, 21.80, Cl, 27.57 Found: C, 46.69; H, 3.97; N, 21.89; Cl, 27.33

Method B

To a stirred suspension of 2-hydroxy-4-methylpyrimidine hydrochloride (6.57 g, 44.8 mmol) in absolute EtOH (200 ml) was added a solution of freshly prepared sodium ethoxide (44.8 mmol) in absolute EtOH (200 ml) and the mixture was stirred at room temperature for 1 hour. The cloudy solution was evaporated to dryness in vacuo and the residue was dried by azeotropic distillation from toluene. Freshly distilled $POCl_3$ (25 ml) was added and the mixture was heated under reflux under $N_2$ for 1 hour. The volatiles were removed by distillation and the remaining syrup was poured onto ice-$H_2O$. Ammonium hydroxide was added until the pH was 11 and the mixture was extracted with $CH_2Cl_2$ (7×75 ml). The pooled organic layers were dried ($MgSO_4$), filtered and evaporated to dryness to give a brown colored, tlc pure product. This was purified on a column of silica gel 60 (4.0×120 cm) developed first with $CH_2Cl_2$ and then $CH_2Cl_2$:MeOH (98:2). Fractions containing the required product were pooled and evaporated to dryness to the title compound as a pale yellow crystalline material which was identical to that prepared in Method A (above).

(b) 4-Methyl-2-[1-[4-methylpiperazinyl)]pyrimidine dihydrochloride

2-Chloro-4-methylpyrimidine (500 mg, 3.89 mmol) and N-methylpiperazine (1.95 g, 19.45 mmol) were mixed in i amyl alcohol (30 ml) and heated overnight under reflux under $N_2$. The mixture was evaporated to dryness and the residue was dissolved in $CH_2Cl_2$ (30 ml), extracted with 10% aqueous $Na_2CO_3$ (5 ml), dried ($MgSO_4$), filtered and evaporated to dryness to give 731 mg of crude product. This was dissolved in $CH_2Cl_2$ and purified on a silica gel 60 column (3×10 cm) developed with $CH_2Cl_2$ and then $CH_2Cl_2$-MeOH (98:2). Fractions containing the required product were pooled and evaporated to dryness to give the product, as a free base. This was dissolved in EtOH (2 ml) and excess ethanolic HCl was added. The precipitated product was isolated by centrifugation (after standing 2 days) and washed with cold EtOH and then $Et_2O$, and dried in vacuo to give the title compound. Mass spec. showed M+ (free base) at 192 m/e.

Calculated for $CH_{16}N_6.2HCl$: C, 45.29; H, 6.84; N, 21.13. Found: C, 45.09; H, 6.81; N, 20.99.

EXAMPLE 6 of 6-(1-butyl)-4-methyl-2-(1-piperazinyl)-pyrimidine dihydrochloride (a) 1-Triphenylmethylpiperazine Piperazine (5.0 g, 58.04 mmol) was dissolved in $CHCl_3$ (100 ml) and $Et_3N$ (9 ml, 64.6 mmol) was added. This solution was heated to reflux and a solution of triphenylmethyl chloride (16.36 g, 58.68 mmol) in $CHCl_3$ (100 ml) was added dropwise, via the reflux condenser, over a period of 4 hours. The reflux was then continued for 3 hours more and then was cooled and allowed to stand at room temperature overnight. A solid precipitated and was filtered off. The filtrate was evaporated to dryness to an oil which was partitioned between 10% aqueous $Na_2CO_3$ (150 ml) and $CHCl_3$ (150 ml). The aqueous layer was washed with two additional portions of $CHCl_3$ (2×150 ml) and the pooled organic layers were dried ($MgSO_4$), filtered and evaporated to dryness to give a straw-colored syrup. This was purified on a silica gel 60 column (800 g) wet packed in $CHCl_3$ and then developed with $CHCl_3$:MeOH (9:1) and then $CHCl_3$:MeOH (4:1). Fractions containing the required product were pooled and evaporated to dryness to give the title compound. Mass spec showed M+ at m/e 328. NMR ($CDCl_3$, $\delta$ from TMS): 3.04 (br) piperazine methylenes; 7.06–7.58 (m) aromatics.

(b) 4-methyl-2-[1-(4-triphenylmethyl)piperazinyl]-pyrimidine

2-Chloro-4-methylpyrimidine (example 5(a)) (0.512 g, 4 mmol) was dissolved in i-amyl alcohol (20 ml) and 1-triphenylmethylpiperazine (1.29 g, 4 mmol) was added followed by $Et_3N$ (1.54 ml, 11 mmol). This solution was heated at 100° overnight and then allowed to cool to room temperature. The precipitated material was filtered off and then partitioned between $CHCl_3$ and $H_2O$. After the pH of the aqueous layer was adjusted to 11.0 using 2.5N NaOH, the layers were separated and the aqueous layer was re extracted with $CHCl_3$. The pooled organic layers were washed with saturated aqueous NaCl, dried over $MgSO_4$, filtered and evaporated to dryness to give the title compound as a tlc and NMR pure product.

(c)
6-(1-Butyl)-4-methyl-2-[1-(4-triphenylmethyl)-piperazinyl]pyrimidine

4-Methyl-2-[1-(4-triphenylmethyl)piperazinyl]-pyrimidine (204 mg, 485 μmol) was dissolved in purified THF (15 ml) and N,N,N',N'-tetramethylethylene diamine (0.08 ml) was added, followed by 2.6M butyl lithium in hexane (0.2 ml). After 30 minutes at room temperature, the mixture was heated to gentle reflux and the heating was continued overnight. $H_2O$ (5 ml) was added and the heating was continued for an additional 15 minutes before the mixture was evaporated to dryness in vacuo. The residue was extracted with $CHCl_3$ and the extract was dried ($MgSO_4$), filtered and evaporated to dryness before being purified on two 20 cm×20 cm×1500 silica gel FG plates developed with water saturated $CH_2Cl_2$.

(d) 6-(1-Butyl)-4-methyl-2-(1-piperazinyl)pyrimidine dihydrochloride

The material prepared in part (c) (105 mg, 0.22 mmol) was treated with a solution of acetone:concentrated HCl (50:1, 5 ml). After 4 hours the suspension was concentrated to dryness and the residue was partitioned between $Et_2O$ and $H_2O$. The aqueous phase was washed with $H_2O$, then 5N NaOH was added and the basic solution was extracted with $CHCl_3$. The $CHCl_3$ phases were pooled, dried ($MgSO_4$) filtered and evaporated to dryness. This residue was treated with ethanolic HCl (1.5 ml) and then evaporated to dryness several times from EtOH, finally in vacuo to give the title compound as a glossy syrup. Mass spec. (EI) shows $M^+$ (free base) at 234.

EXAMPLE 7

Preparation of 4-(2-Butyl)-2-(1-piperazinyl)pyrimidine dihydrochloride (a) 2-[1-(4-Triphenylmethyl)piperazinyl]pyrimidine 2-(1-Piperazinyl)pyrimidine dihydrochloride (10.0 g, 42.17 mmol) was suspended in $CHCl_3$ (100 ml) and $Et_3N$ (25 ml) was added followed by triphenylmethyl chloride (11.9 g, 42.69 mmol). This mixture was well stirred under reflux under nitrogen overnight and was then cooled to room temperature. The insoluble $CH_2Cl_2$ and dried to give the title compound which was contaminated with a small amount of triethylammonium hydrochloride. This material was partitioned between $CHCl_3$ and $H_2O$ and the organic phase was dried ($MgSO_4$), filtered and evaporated to dryness to give material suitable for further synthetic transformations. Mass spec. shows at a m/e 408.

Calculated for $C_{27}H_{26}H_4$: C, 79.77; H, 6.45; N, 13.78. Found: C, 79.14; H, 6.32; N, 13.40.

(b)
4-(2-Butyl)-2-[1-(4-triphenylmethyl)piperazinyl]pyrimidine

2-[1-(4-Triphenylmethyl)piperazinyl]pyrimidine (425 mg, 104 mmol) was dissolved in purified THF (20 ml)—some warming was necessary—and then (after cooling to room temperature) N,N,N',N'-tetramethyl ethylene diamine (0.18 ml) was added, followed by 1.3M sec butyllithium in cyclohexane (0.8 ml). The mixture was heated overnight under reflux and after a total reaction time of 20 hours, $H_2O$ (5 ml) was added and the heating was continued for another 20 minutes. The reaction was evaporated to dryness and the residue was partitioned between $CHCl_3$ and $H_2O$. The organic phase was dried ($MgSO_4$), filtered, and concentrated to dryness and then was purified on a column (100 g) of Baker basic aluminum oxide (Brockman Activity, grade 1) packed in cyclohexane. The column was developed with EtOAc cyclohexane (1:49) and fractions containing the required product were pooled and evaporated to dryness to give the title compound.

(c) 4-(2-Butyl)-2-(1-piperazinyl)pyrimidine dihydrochloride

The material prepared in part (b) was treated with 7 ml of a solution of acetone concentrated HCl (60:1) and second phase started to separate after several minutes. The mixture was evaporated to dryness and the residue was partitioned between $H_2O$ (15 ml) and ether (20 ml). The aqueous phase was washed with ether, then made alkaline by addition of 5N NaOH and further extracted with $CHCl_3$ (2×20 ml). The pooled $CHCl_3$ layers were dried ($MgSO_4$), filtered and evaporated to dryness. This residue was treated with ethanolic HCl (115 mg HCl in 2 ml EtOH) and concentrated to dryness several times in vacuo from EtOH to give the title compound as a glassy syrup. Mass spec. (EI) shows $M^+$ (free base) at 220.

EXAMPLE 8

Preparation of
2-Methyl-5-methoxy-4-(1-piperazinyl)pyrimidine dihydrochloride (a) 4-Hydroxy-2-methyl-5-methoxypyrimidine To a mixture of sodium-dried $Et_2O$ (300 ml) and sodium pellets (4.88 g, 0.212 mol) in a 3 necked flask, filted with a reflux condenser and a mechanical stirrer, and all under $N_2$, was added dropwise over 1 hour a mixture of ethyl methoxy acetate (25 g, 0.212 mol) and ethyl formate (23.5 g, 0.23 mol). Refluxing commenced after ~1 hour and was allowed to continue for an additional 30 minutes. A reddish thick gum came out of solution and this was kept overnight under $N_2$. The solvent was decanted off and the gum was washed with 3 portions of $Et_2O$. Absolute EtOH (250 ml) was added followed by acetamidine hydrochloride (20 g, 0.212 mol). This mixture was stirred and heated under reflux for 6 hours. The mixture was cooled and the precipitated salts were filtered off and the filtrate was evaporated to dryness. This residue was dissolved in $H_2O$ and the pH was adjusted to 4 with acetic acid (final volume, 200 ml). No precipitation occurred, even on cooling, and the solution was concentrated to approximately 40 ml when the precipitated material was filtered off and air dried. This material was tlc pure [silica, $CH_2Cl_2$-MeOH (95:5)] and mass spec. showed $M^+$ at 140 m/e.

(b) 4-Chloro-2-methyl-5-methoxypyrimidine

The material prepared in part (a) (4.0 g, 8.5 mmol) was placed in a round bottomed flask and distilled POCl₃ (12 ml) was added carefully. This mixture was heated under reflux under N₂ until dissolution had occurred (approximately 30 minutes) and then for an additional 45 minutes. The excess POCl₃ was removed by distillation and the remaining material was passed onto ice-H₂O. This mixture was then rendered basic by the addition of NH₄OH and the precipitate which formed was filtered off and air-dried. An additional amount of product was obtained by extraction of the filtrate with CHCl₃ NMR (CDCl₃, δ from TMS): 2.67 (S, CH₃), 4.01 (S, OCH₃), 8.25 (S, H₆).

Calculated for $C_6H_7N_2ClO$: C, 45.44; H, 4.45; N, 17.66 Found: C, 45.24; H, 4.59; N, 17.47.

(c) 4-[1-(4-BOC)piperazinyl]-2-methyl-5-methoxypyrimidine

The material prepared in part (b) (1.4 g, 8.8 mmol) and (1-BOC)piperazine (7.44 g, 399 mmol) were dissolved in i-amyl alcohol (50 ml) and heated under reflux under N₂ for 1 hour. After cooling to room temperature, insoluble non-unabsorbing material was filtered off and the filtrate was evaporated in vacuo to a syrup. This was partitioned between CH₂Cl₂ (50 ml) and 10% aqueous Na₂CO₃ (10 ml). The organic phase was extracted 3 more times with 10% aqueous Na₂CO₃ (3×30 ml), H₂O (1×30 ml), dried (MgSO₄), filtered and evaporated to dryness. This crude product was purified on a silica gel 60 column (4×7 cms) developed with EtOAc, and overlapping fractions were rechromatographed using acetone for developing. Fractions from both columns containing pure product were pooled and evaporated to dryness to give the title compound as off-white crystals.

Calculated for $C_{15}H_{24}N_4O_3$: C, 58.42; H, 7.84; N, 18.17. Found: C, 58.60; H, 7.61; N, 18.06.

(d) 2-Methyl-5-methoxy-4-(1-piperazinyl)pyrimidine dihydrochloride

The material prepared in part (c) (970 mg, 3.15 mmol) was dissolved in CF₃COOH (15 ml) and allowed to stand at room temperature for 1 hour. This solution was then blown down under a nitrogen stream and the residue was evaporated to dryness several times from MeOH and then H₂O. The residue was dissolved in a little H₂O and then passed down a Dowex 1×2 (OH) resin 12.6×20 cm column), developed with H₂O. Fractions containing the required product (as free base) were pooled and evaporated to dryness and the residue was dissolved in absolute EtOH (2 ml) and methanolic HCl was added. After standing overnight, no observable crystallization had occurred and the solution was concentrated under a nitrogen stream. Product precipitated and was collected by centrifugation and then washed with chilled absolute EtOH and then Et₂O, before being dried in vacuo.

Calculated for $C_{10}H_{18}N_4OCl_2$: C, 42.71; H, 6.45; N, 19.93. Found: C, 42.77; H, 6.35; N, 19.96.

EXAMPLE 9

Preparation of 2-Methyl-4-(1-piperazinyl)-S-triazine dihydrochloride

(a) 2-[1-(4-BOC)piperazinyl)]-4-methyl-S-triazine

2-[1-(4-BOC)piperazinyl)]-6-chloro-4-methyl-S-triazine (216 mg, 0.780 mmol) was dissolved in EtOH (20 ml) and hydrogenated over 5% Pd/C in the presence of MgO (120 mg). The mixture was filtered through Supercel and the filtrate was evaporated to dryness. This residue was partitioned between CHCl₃ and H₂O and the organic phase was dried (MgSO₄), filtered and evaporated to dryness. This crude product was purified by chromatography on silica gel 60 (2×7 cm) developed with EtOAc cyclohexane (1:1). Fractions containing the required product were pooled and evaporated to dryness to give the title compound.

(b) 2-Methyl-4-(1-piperazinyl)-S-triazine dihydrochloride

The material prepared in part (a) was dissolved in EtOH (10 ml) and ethanolic HCl (5 ml) was added. This mixture was concentrated to 3 ml under a stream of N₂ and the precipitated product was isolated by centrifugation and washed with EtOH.

Calculated for $C_8H_{13}N_5$ 2HCl 0.73 H₂O: C, 36.23; H, 6.26; N, 26.41; Cl, 26.73. Found: C, 36.65; H, 6.31; N, 26.11; Cl, 26.37.

EXAMPLE 10

Preparation of 2-Amino-4-(1-piperazinyl)-6-methylpyrimidine

(a) 2-Amino-4-[1-(4-piperazinecarboxaldehyde)]-6-methylpyrimidine 5.00 g of 2-amino-4-chloro-6-methyl-pyrimidine (Aldrich) (34.84 mmol) was dissolved in hot isoamyl alcohol (100 ml) at 130°. 1-Piperazinecarboxaldehyde (Aldrich), 14.37 ml (15.91 g; 139.36 mmol) was added and the solution was refluxed for 5 hours under N₂ (tlc, 5% MeOH-CH₂Cl₂ showed no starting material) and then cooled to 0° overnight. The solid which formed was filtered off and washed with Et₂O. NMR (60 MHz) indicated some contamination with piperazine carboxyldehyde (or HCl salt) and the material was recrystallized from EtOH (100 ml) to give the title compound. This product was recrystallized from H₂O with slow cooling.

Calculated for $C_{10}H_{15}N_5O_1$: C, 54.28; H, 6.83, N, 31.65. Found: C, 53.78; H, 6.73; N, 31.20. Calculated for $C_{10}H_{15}N_5O_1.0.2H_2O$: C, 53.41; H, 6.90; N, 31.15.

(b) 2-Amino-4-(1-piperazinyl)-6-methylpyrimidine 0.5068 g (2.29 mmol) of the product from (a) was dissolved in 2N HCl (15 ml) and heated at 100°, under a condenser for 1½ hour and the r×n was then cooled and evaporated to dryness, in vacuo (2× from H₂O). The white solid was crystallized from absolute EtOH containing a trace of H₂O to give white crystals.

Anal. Cal. $C_9H_{17}N_5Cl_2 0.75H_2O$: C, 38.65; H, 6.67; N, 25.04; Cl, 25.35. Found: C, 38.92; H, 6.56; N, 25.31; Cl, 25.08.

TABLE 1[a]

NMR SHIFT DATA FOR PIPERAZINYLPYRIMIDINES

| EXAMPLE | PIPERAZINE METHYLENE RESONANCES | HETEROCYCLIC PROTONS | OTHERS |
|---|---|---|---|
| 1a[i] | 3.45(m), 3.83(m) | 6.46(s) | 1.50(s), $C(CH_3)_3$ |
|  |  |  | 2.32(s), $CH_3$ |
| 1b[i] | 3.47(m), 3.79(m) | 6.38(d), 8.14(d) | 1.47(s), $C(CH_3)_3$ |
|  |  |  | 2.32(s), $CH_3$ |
| 1c[ii] | 3.38(m), 4.05(m) | 6.81(d), 8.26(d) | 2.44(s), $CH_3$ |
| 2a[i] | 3.48(m), 3.76(m) | — | 1.49(s), $C(CH_3)_3$ |
|  |  |  | 2.19(s), $CH_3$ |
|  |  |  | 2.37(s), $CH_3$ |
| 2b[i] | 3.48(m), 3.75(m) | 7.98(s) | 1.49(s), $C(CH_3)_3$ |
|  |  |  | 2.09(s), $CH_3$ |
|  |  |  | 2.32(s), $CH_3$ |
| 2c[ii] | 3.35(m), 3.97(m) | 8.09(s) | 2.14(s), $CH_3$ |
|  |  |  | 2.38(s), $CH_3$ |
| 3a[i] | 3.46(m), 3.78(m) | 6.28(s) | 1.48(s), $C(CH_3)_3$ |
|  |  |  | 2.28(s), $CH_3$'s |
| 3b[ii] | 3.42(m), 4.14(m) | 6.81(s) | 2.47(s), $CH_3$'s |
| 4c[i] | 3.49(m), 3.76(m) | — | 1.49(s), $C(CH_3)_3$ |
|  |  |  | 2.08(s), 5-$CH_3$ |
|  |  |  | 2.32(s), 4,6-$CH_3$'s |
| 4d[ii] | 3.43(m), 4.14(m) | — | 2.17(s), 5-$CH_3$ |
|  |  |  | 2.52(s), 4,6-$CH_3$'s |
| 5b[ii] | 3.14–3.80(m's) | 6.94(d), 8.29(d) | 2.53(s), $CH_3$ |
|  |  |  | 3.00(s), $CH_3$ |
| 6b[i] | 2.00–2.60(b), | 6.30(d), 8.09(d) | 2.28(s) $CH_3$ |
|  | 3.62–4.12(b) |  | 7.08–7.66(m) aromatic |
| 6c[i] | 2.14–2.60(b) | 6.22(s) | 0.90(t), $CH_3$ |
|  | 3.68–4.14(b) |  | 1.33(m), —$CH_2$— |
|  |  |  | 1.50–1.74(m), —$CH_2$— |
|  |  |  | 2.14–2.60(m), —$CH_2$—, and $CH_3$ |
|  |  |  | 7.08–7.70(m), aromatics |
| 6d[iii] | 3.48(m), 4.22(m) | 6.93(s) | 0.94(t) $CH_3$ |
|  |  |  | 1.40(m) —$CH_2$— |
|  |  |  | 1.74(m) —$CH_2$— |
|  |  |  | 2.55(s) $CH_3$ |
|  |  |  | 2.83(m) —$CH_2$— |
| 7a[i] | 2.14–2.60(b), | 6.43(t), 8.24d | 7.10–7.76(m) aromatic |
|  | 3.72–4.08(b) |  |  |
| 7b[i] | 2.14–2.80(b) | 6.30(d), 8.12(d) | 0.82(t) $CH_3$ |
|  | 3.82–4.28(b) |  | 1.17(d) $CH_3$ |
|  |  |  | 1.40–1.64(m) —$CH_2$— |
|  |  |  | 2.24–2.60(m) —CH— |
|  |  |  | 7.07–7.78(m) aromatic |
| 7c[ii] | 3.47(m), 4.17(m) | 7.10(d), 8.29(d) | 0.88(t) $CH_3$ |
|  |  |  | 1.29(d) $CH_3$ |
|  |  |  | 1.60–1.86(m) —$CH_2$— |
|  |  |  | 2.80–2.94(m) —CH— |
| 8c[i] | 3.52(m), 3.67(m) | 7.82(s) | 1.45(s), $C(CH_3)_3$ |
|  |  |  | 2.46(s), $CH_3$ |
|  |  |  | 3.82(s), $OCH_3$ |
| 8d[ii] | 3.45(m), 4.37(m) | 7.92(s) | 2.57(s), $CH_3$ |
|  |  |  | 3.94(s), $OCH_3$ |
| 9a[i] | 3.47(m), 3.84(m) | 8.44(s) | 1.48(s), $C(CH_3)_3$ |
|  |  |  | 2.42(s), $CH_3$ |
| 9b[ii] | 3.49(m), 4.36(m) | 8.76(s) | 2.62(s), $CH_3$ |
| 10a[iii] | 3.46(m), 3.60(m) | 6.12(s) | 2.14(s), $CH_3$ |
|  |  |  | 6.34(brS), $NH_2$ |
|  |  |  | 8.14(s), CHO |
| 10b[ii] | 3.42(m), 4.10(m) | 6.39(s) | 2.35(s), $CH_3$ |

[a]All chemical shifts measured in δppm downfield from either TMS ($CDCL_3$ or $d_6$-DMSO solvents) or TSP ($D_2O$ solvent)

Solvents:
[i]$CDCl_3$
[ii]$D_2O$
[iii]$d_6$-DMSO

What is claimed is:

1. A compound of structural formula I

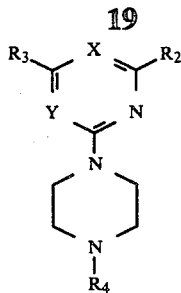

(I)

wherein

X and Y are independently —N= and —(C—$R_1$)=; provided that at least one of X or Y is —N= and that when X is —N=, $R_1$ is other than H, alkyl or alkoxy;

$R_1$ is H, $C_{1-6}$alkyl, halo$C_{1-6}$alkyl, dihalo$C_{1-6}$alkyl or $C_{1-6}$alkoxy;

$R_2$ and $R_3$ are independently H, $C_{1-6}$alkyl, halo$C_{1-6}$alkyl, dihalo$C_{1-6}$alkyl, or $NH_2$, or $NR_5R_6$, or $C_{1-6}$alkoxy; provided that only one of $R_2$ and $R_3$ may be H and when $R_2$ or $R_3$ is $NH_2$ or $NR_5R_6$ X is —N=;

$R_4$ is H, $C_{1-6}$alkyl, $C_{6-10}$aryl$C_{1-6}$alkyl, $C_{2-6}$alkenyl, $C_{2-6}$alkynyl;

$R_5$ and $R_6$ are independently H, $C_{1-6}$alkyl, or $R_5$ and $R_6$ together with the nitrogen atom to which they are attached form a hetero cyclic ring of 5 to 6 atoms; and halo is Br, Cl or F;

and the pharmaceutically acceptable salts thereof.

2. A compound of claim 1 wherein:
X is —(C—$R_1$)=;
Y is —N=.

3. A compound of claim 2 wherein:
$R_1$ is H, $C_{1-6}$alkyl, F$C_{1-6}$alkyl or $F_2C_{1-6}$alkyl;
$R_2$ is H, $C_{1-6}$alkyl, F$C_{1-6}$alkyl, or $F_2C_{1-6}$alkyl;
$R_3$ is H, $C_{1-6}$ alkyl, F$C_{1-6}$alkyl or $F_2C_{1-6}$alkyl; provided that only one of $R_2$ and $R_3$ is H.
$R_4$ is H or $C_{1-6}$alkyl.

4. A compound of claim 3 wherein:
F$C_{1-6}$alkyl is $FCH_2CH_2$—; and
$F_2C_{1-6}$alkyl is $F_2CHCH_2$—.

5. A compound of claim 4 wherein:
$R_1$ is H or $C_{1-6}$alkyl;
$R_2$ is H or $C_{1-6}$alkyl;
$R_3$ is H or $C_{1-6}$alkyl; provided that only one of $R_2$ and $R_3$ may be H.

6. A compound of claim 5 wherein:
$R_1$ is H or $CH_3$;
$R_2$ is $C_{1-6}$alkyl.

7. A compound of claim 6 selected from the group wherein:
a. $R_1$=H, $R_2$=n butyl, $R_3$=methyl and $R_4$=H;
b. $R_1$=H, $R_2$=sec-butyl, $R_3$=H, and $R_4$=H;
c. $R_1$=methyl, $R_2$=methyl, $R_3$=H, and $R_4$=H;
d. $R_1$=H, $R_2$=methyl, $R_3$=H, and $R_4$=H;
e. $R_1$=H, $R_2$=methyl, $R_3$=methyl and $R_4$=H;
f. $R_1$=H, $R_2$=methyl, $R_3$=H, and $R_4$=methyl;
g. $R_1$=methyl, $R_2$=methyl, $R_3$=methyl, $R_4$=H.

8. A compound of claim 1 wherein:
X is —N=;
Y is —(C—$R_1$)=.

9. A compound of claim 8 wherein:
$R_1$ is F$C_{1-6}$alkyl or $F_2C_{1-6}$alkyl;
$R_2$ is H or $C_{1-6}$alkyl, F$C_{1-6}$alkyl, $F_2C_{1-6}$alkyl or $NH_2$ or $NR_5R_6$;
$R_3$ is H or $C_{1-6}$alkyl, F$C_{1-6}$alkyl, $F_2C_{1-6}$alkyl; provided that only one of $R_2$ and $R_3$ may be H;
$R_4$ is H or $C_{1-6}$alkyl.

10. A compound of claim 9 wherein:
$R_2$ is H or $C_{1-6}$alkyl or $NH_2$ or $NR_5R_6$;
$R_3$ is H or $C_{1-6}$alkyl.

11. A compound of claim 10 wherein:
$R_2$ is or $NH_2$; and
$R_4$ is H.

12. A compound of claim 1 wherein:
X is —N=;
Y is —N=.

13. A compound of claim 12 wherein:
$R_2$ is H or $C_{1-6}$alkyl, F$C_{1-6}$alkyl or $F_2C_{1-6}$alkyl;
$R_3$ is H or $C_{1-6}$alkyl, F$C_{1-6}$alkyl, or $F_2C_{1-6}$alkyl; and
$R_4$ is H or $C_{1-6}$alkyl.

14. A compound of claim 13 wherein
$R_2$ is H or $C_{1-6}$alkyl; and
$R_3$ is H or $C_{1-6}$alkyl.

15. A compound of claim 14 wherein
$R_2$ is methyl, $R_3$ is H, $R_4$ is H.

16. A composition useful for the treatment of diabetes or obesity with associated insulin resistance which consists of an inert carrier and a nontoxic dose of a compound of claim 1.

17. A method for the treatment of diabetes or obesity with associated insulin resistance which consists of orally administering to a patient in need of such treatment a therapeutically effective nontoxic dose of a compound of claim 1.

18. A composition useful for the treatment of diabetes or obesity with associated insulin resistance which consists of an inert carrier and a nontoxic dose of a compound of claim 7.

19. A method for the treatment of diabetes or obesity with associated insulin resistance which consists of orally administering to a patient in need of such treatment a therapeutically effective nontoxic dose of a compound of claim 7.

20. A composition useful for the treatment of diabetes or obesity with associated insulin resistance which consists of an inert carrier and a nontoxic dose of a compound of claim 11.

21. A method for the treatment of diabetes or obesity with associated insulin resistance which consists of orally administering to a patient in need of such treatment a therapeutically effective nontoxic dose of a compound of claim 11.

22. A composition useful for the treatment of diabetes or obesity with associated insulin resistance which consists of an inert carrier and a nontoxic dose of a compound of claim 15.

23. A method for the treatment of diabetes or obesity with associated insulin resistance which consists of orally administering to a patient in need of such treatment a therapeutically effective nontoxic dose of a compound of claim 15.

* * * * *